United States Patent
Hussain et al.

(10) Patent No.: US 11,327,063 B2
(45) Date of Patent: May 10, 2022

(54) SENSOR SYSTEM, METHOD OF PRODUCTION, AND SENSOR DEPLOYMENT SYSTEM

(71) Applicant: KING ABDULLAH UNIVERSITY OF SCIENCE AND TECHNOLOGY, Thuwal (SA)

(72) Inventors: Muhammad Mustafa Hussain, Austin, TX (US); Joanna Mohammad Nassar, Thuwal (SA); Sherjeel Khan, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 188 days.

(21) Appl. No.: 16/632,113

(22) PCT Filed: Aug. 20, 2018

(86) PCT No.: PCT/IB2018/056293
§ 371 (c)(1),
(2) Date: Jan. 17, 2020

(87) PCT Pub. No.: WO2019/077417
PCT Pub. Date: Apr. 25, 2019

(65) Prior Publication Data
US 2020/0173972 A1  Jun. 4, 2020

Related U.S. Application Data

(60) Provisional application No. 62/633,641, filed on Feb. 22, 2018, provisional application No. 62/572,770, filed on Oct. 16, 2017.

(51) Int. Cl.
*G01N 33/00* (2006.01)
*A01G 7/00* (2006.01)
(Continued)

(52) U.S. Cl.
CPC .......... *G01N 33/0098* (2013.01); *A01G 7/00* (2013.01); *B64D 1/02* (2013.01); *G01K 7/16* (2013.01);
(Continued)

(58) Field of Classification Search
CPC ........ G01N 33/0098; A01G 7/00; B64D 1/02; G01K 7/16; G01L 1/22
See application file for complete search history.

(56) References Cited

U.S. PATENT DOCUMENTS 9,209,083 B2   12/2015  Hussain et al.
9,513,271 B2 * 12/2016  Okumura ............. G01N 33/246
(Continued)

FOREIGN PATENT DOCUMENTS

EP    2056771 A1      5/2009
JP    2012137354 A *  7/2012
(Continued)

OTHER PUBLICATIONS

Amjadi, M. et al., "Highly Stretchable and Sensitive Strain Sensor Based on Silver Nanowire-Elastomer Nanocomposite," ACS NANO, Apr. 21, 2014, vol. 8, No. 5, pp. 5154-5163.
(Continued)

*Primary Examiner* — Jamel E Williams
(74) *Attorney, Agent, or Firm* — Patent Portfolio Builders PLLC (57) ABSTRACT

A sensor system includes a plant growth sensor, an environmental sensor device, and processing electronics. The plant growth sensor includes a strain sensor arranged on a first stretchable and flexible substrate. The environmental sensor device includes first and second environmental sensors arranged on a second stretchable and flexible substrate. The processing electronics are electrically coupled to the plant growth sensor and the environmental sensor device.
(Continued)

The processing electronics include a wireless communication transceiver.

19 Claims, 10 Drawing Sheets

(51) Int. Cl.
| | |
|---|---|
| B64D 1/02 | (2006.01) |
| G01K 7/16 | (2006.01) |
| G01L 1/22 | (2006.01) |
| G01N 27/22 | (2006.01) |
| H04B 1/3827 | (2015.01) |

(52) U.S. Cl.
CPC .............. *G01L 1/22* (2013.01); *G01N 27/223* (2013.01); *H04B 1/3827* (2013.01)

(56) References Cited

U.S. PATENT DOCUMENTS

| | | | |
|---|---|---|---|
| 9,520,293 | B2 | 12/2016 | Hussain et al. |
| 9,582,873 | B2 | 2/2017 | Ulman |
| 2016/0033943 | A1 | 2/2016 | King et al. |
| 2018/0242531 | A1* | 8/2018 | Berry, III ............... A01G 27/02 |
| 2019/0231267 | A1* | 8/2019 | Oren .................... A61B 5/6806 |
| 2020/0302338 | A1* | 9/2020 | Carroll ................... G06N 20/00 |

FOREIGN PATENT DOCUMENTS

| | | |
|---|---|---|
| KR | 20160135458 A | 11/2016 |
| WO | 2004109238 A1 | 12/2004 |
| WO | 2015179320 A1 | 11/2015 |
| WO | 2017122178 A1 | 7/2017 |

OTHER PUBLICATIONS

Anderson, P.M. et al., "Growth and Development Guide for Spring Barley," Small Grains Production, https://www.extension.umn.edu/agriculture/small-grains/growth-and-development/spring-barley/#fig10, 2013, downloaded from the Internet Mar. 8, 2018, Regents of the University of Minnesota.

Biology Junction, Plant Structure Bi, http:www.biologyjunction.com/plant_structure_bi1.htm, downloaded from the Internet Mar. 8, 2018.

Botfeeder, ABS and PLA Comparison Table, https://www.botfeeder.ca/abs-vs-pla/, downloaded from the Internet Mar. 8, 2018.

Dai, C.-L., "A Capacitive Humidity Sensor Integrated with Micro Heater and Ring Oscillator Circuit Fabricated by CMOS-MEMS Technique," Sensors and Actuators B, Mar. 2007, vol. 122, pp. 375-380, Elsevier.

Dole, J.M. et al. "Floriculture: Principles and Species," HortTechnology, Book Reviews, Apr.-Jun. 1999.

Harada, S. et al., "Fully Printed, High Sensitive Multifunctional Artificial Electronic Whisker Arrays Integrated with Strain and Temperature Sensors," ACS NANO, Mar. 12014, vol. 8, No. 4, pp. 3921-3927.

Hocheng, H. et al., "Design, Fabrication and Failure Analysis of Stretchable Electrical Routings," Sensors, Jul. 4, 2014, vol. 14, pp. 11855-11877.

International Search Report in corresponding/related International Application No. PCT/IB2018/056293, dated Jan. 28, 2019.

James, J. et al., "Plant Growth Monitoring System, with Dynamic User-Interface," IEEE 2016 Humanitarian Technology Conference (R10-HTC), Dec. 21-23, 2016, pp. 1-5, IEEE.

Jou, J.-H. et al., "Adhesion of Polyimide to Silicon and Polyimide," Journal of Applied Polymer Science, Feb. 15, 1993, vol. 47, pp. 1219-1232, John Wiley & Sons, Inc.

Kang, D. et al., Ultrasensitive Mechanical Crack-Based Sensor Inspired by the Spider Sensory System, Nature, Dec. 11, 2014, vol. 516, pp. 222-226, Macmillan Publishers Limited.

Körner, O., "Processed-Based Humidity Control Regime for Greenhouse Crops," Computers and Electronics in Agriculture, Aug. 2003, vol. 39, pp. 173-192, Elsevier.

Lee, C.-Y. et al., "Fabrication of Micro Sensors on a Flexible Substrate," Sensors and Actuators A: Physical, May 13, 2008, vol. 147, pp. 173-176.

Meng, R. et al., Growth Curve Registration for Evaluating Salinity Tolerance in Barley, Plant Methods, Mar. 23, 2017, vol. 13, No. 18.

Mortensen, L.V., "Effects of Air Humidity on Growth, Flowering, Keeping Quality and Water Relations of Four Short-Day Greenhouse Species," Scientia Horticulturae, Dec. 2000, vol. 86, pp. 299-300, Elsevier.

Nasa, "The Lift Equation," https://www.grc.nasa/gov/www/k-12/airplane/lifteq.html, downloaded from the Internet Mar. 8, 2018.

Nassar, J.M. et al., "From Stretchable to Reconfigurable Inorganic Electronics," Extreme Mechanics Letters, May 6, 2016, vol. 9, pp. 245-268, Elsevier.

Parrot Flower Power, http://global.parrot.com/au/products/flower-power, downloaded from the Internet Mar. 8, 2018.

Parrot Pot, http://www.parrot.com/us/commected-garden/parrot-pot#in-the-box, downloaded from the Internet Mar. 8, 2018.

Paulitz, T.C. et al., "Biological Control in Greenhouse Systems," Annual Review of Phytopathology, Sep. 2001, vol. 39, pp. 103-133.

Peery, J., "How Does Humidity Influence Crop Quality?," PRO-MIX, https://www.pthorticulture.com/en/training-center/how-does-humidity-influence-crop-quality/, downloaded from the Internet Mar. 8, 2018.

Plantlink, http://myplantlink.com, downloaded from the Internet Mar. 8, 2018.

Sánchez-Blanco, J., "Effects of Irrigation and Air Humidity Preconditioning on Water Relations, Growth and Survival of Rosmarinus Officinalis Plants During and After Transplanting," Journal of Plant Physiology, Oct. 18, 2004, vol. 161, pp. 1133-1142, Elsevier.

Shelton S., "Sweating High Humidity," Greenhouse Product News, https://gpnmag.com/article/sweating-high-humidity/, downloaded from the Internet Mar. 8, 2018.

Sunkar, R., "Plant Stress Tolerance," Methods in Molecular Biology, Jun. 1, 2010, vol. 639, 401, Springer.

Tai, W.-C. et al., "Development of a Multi-Parameter Plant Growth Monitoring and Control System for Quality Agriculture Application," Proceedings of the 2017 IEEE International Conference on Applied Systems Innovation (IEEE-ICASI 2017), May 13-17, 2017, pp. 1130-1133.

Tang, W. et al., "Rapid Fabrication of Flexible and Stretchable Strain Sensor by Chitosan-Based Water Ink for Plants Growth Monitoring," Advanced Materials Technology, May 2017, vol. 2, pp. 1700021 (1-5), WILEY-VCH Verlag GmbH & Co.

Tetelin, A. et al., "Fast Response Humidity Sensors for a Medical Microsystem," Sensors and Actuators B, Jun. 2003, vol. 91, pp. 211-218, Elsevier.

Van Straten, G. et al., "Towards User Accepted Optimal Control of Greenhouse Climate," Computers and Electronics in Agriculture, May 2000, vol. 26, Issue 3, pp. 221-238, Elsevier.

Ward B. et al, "A Model-Based Approach to Recovering the Structure of a Plant from Images," European Conference on Computer Vision, Mar. 11, 2015, pp. 215-230, Springer.

Written Opinion of the International Searching Authority in corresponding/related International Application No. PCT/IB2018/056293, dated Jan. 28, 2019.

Yamada, T. et al., "A Stretchable Carbon Nanotube Strain Sensor for Human-Motion Detection," Nature Nanotechnology, May 2011, vol. 6, pp. 296-301.

Yang, T. et al., "Structural Engineering of Gold Thin Films with Channel Cracks for Ultrasensitive Strain Sensing," Materials Horizons, Feb. 26, 2016, vol. 3, pp. 248-255, The Royal Society of Chemistry.

Zampetti E. et al., "Design and Optimization of an Ultra Thin Flexible Capacitive Humidity Sensor," Sensors and Actuators B: Chemical, Sep. 9, 2009, vol. 143, pp. 302,307, Elsevier.

Zhu, J.-K., "Plant Salt Tolerance," Trends in Plant Science, Feb. 2001, vol. 6, No. 2, pp. 66-71.

(56) References Cited

OTHER PUBLICATIONS

Communication pursuant to Article 94(3) EPC in corresponding/related European Application 18769794.1, dated Aug. 13, 2021.

\* cited by examiner

SENSOR SYSTEM, METHOD OF PRODUCTION, AND SENSOR DEPLOYMENT SYSTEM

CROSS-REFERENCE TO RELATED APPLICATIONS

This application is a U.S. National Stage Application of International Application No. PCT/IB2018/056293, which claims priority to U.S. Provisional Patent Application No. 62/572,770, filed on Oct. 16, 2017, entitled "Compliant Plant Sensor," and U.S. Provisional Patent Application No. 62/633,641, filed on Feb. 22, 2018, entitled "Sensor System, Method of Production, and Sensor Deployment System," the disclosures of which are incorporated herein by reference in their entirety.

BACKGROUND

Technical Field

Embodiments of the disclosed subject matter generally relate to a sensor system, method of production, and a sensor deployment system.

Discussion of the Background

Agriculture consumes a significant amount of the Earth's freshwater with some studies concluding that agriculture consumes approximately 70% of the Earth's freshwater. Environmental changes have reduced the available amount of freshwater, and thus freshwater is quickly becoming a precious resource, which increases the overall costs of growing plants.

Conventional techniques for conserving water for growing plants involve monitoring water sensors placed in the soil around plants. These conventional sensors are typically expensive and provide limited information about the overall health of the plants. For example, these sensors provide generalized information about the moisture content of the soil, but do not indicate how much water is being used by any individual plant. This may result in some plants having access to sufficient quantities of water while other proximately-located plants not having access to sufficient quantities of water.

Further, moisture content of soil may not provide sufficient information about the growth of the plant themselves because the moisture content of soil is just one factor impacting plant growth. This can result in overwatering plants, which wastes precious water resources, or underwatering plants, which can result in plant destruction or producing plants that are undersized or have poorly formed shapes that do not correspond to the shapes consumers expect for a particular type of plant.

The micro-climate surrounding a plant has major effect on its health and photosynthesis process, where certain plants struggle in sub-optimal environmental conditions and unbalanced levels of humidity and temperature. A number of abiotic factors such as drought, salinity, excess irrigation, and extreme temperature and humidity levels, can have huge impacts on plant productivity and survival rate of the plants. Factors such as inadequate temperature levels and reduced moisture can obstruct the healthy development of a plant. The ability to remotely track and correlate the effect of local environmental conditions on the healthy growth of plants can have great impact for increasing survival rate of plants and augmenting agriculture output.

Sensors must be deployed in plant fields in order to monitor the plants' healthy growth. Localized information regarding temperature and humidity is more useful than more general information across an entire field of plants. However, localized information requires deployment of more sensors per unit area, which is typically performed manually. Thus, deployment of sensors to provide more localized temperature and humidity information can be very time consuming, costly, and resource intensive.

While monitoring environmental conditions is useful for assessing the effect on plant growth, it is also useful to monitor the growth of the plants themselves. This is currently performed using active imaging systems that capture plant growth via stems and leaf elongations over time. Active imaging systems, however, are complex and costly. Other techniques try to predict and optimize plant growth conditions by adjusting major growth parameters, including environmental temperature, humidity, soil water, and illumination data. However, this data does not reflect definite information from the plant itself.

Thus, it would be desirable to develop environmental sensors that can provide more localized environmental measurements surrounding each plant, including plant growth conditions via physical elongation. Further, it would be desirable to provide for less costly, time and resource consuming ways to deploy environmental sensors. Also, it would be desirable to provide sensors that can measure plant growth without the cost and complications of active imaging systems.

Further, it would be desirable for the widespread distribution of lightweight sensors on the surface of each plant. These sensors should be sufficiently small, compliant, and light enough to be mounted on the leaves without harming the plant, underlining the need for flexible and seamless sensors.

SUMMARY

According to an embodiment, there is a sensor system, which includes a plant growth sensor, an environmental sensor device, and processing electronics. The plant growth sensor includes a strain sensor arranged on a first stretchable and flexible substrate. The environmental sensor device includes first and second environmental sensors arranged on a second stretchable and flexible substrate. The processing electronics are electrically coupled to the plant growth sensor and the environmental sensor device. The processing electronics include a wireless communication transceiver.

According to another embodiment, there is a method of producing a sensor system. A plant growth sensor, which includes a strain sensor arranged on a first stretchable and flexible substrate, is formed. An environmental sensor device, which includes first and second environmental sensors arranged on a second stretchable and flexible substrate, is formed. Processing electronics are coupled to the plant growth sensor and the environmental sensor device. The processing electronics includes a wireless communication transceiver.

According to a further embodiment, there is a sensor deployment system, which includes an airborne vehicle, an environment sensor device, and processing electronics. The airborne vehicle comprises a hollow base and a plurality of wings extending from a top portion of the hollow base. The hollow base and the plurality of wings are monolithic. The environmental sensor device is arranged on an outer surface of the hollow base. The environmental sensor device includes first and second environmental sensors arranged on a stretchable and flexible substrate. The processing electronics are arranged on an inner surface of the hollow base. The processing electronics are coupled to the environmental sensor device and the processing electronics includes a wireless communication transceiver.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of environmental and plant monitoring.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
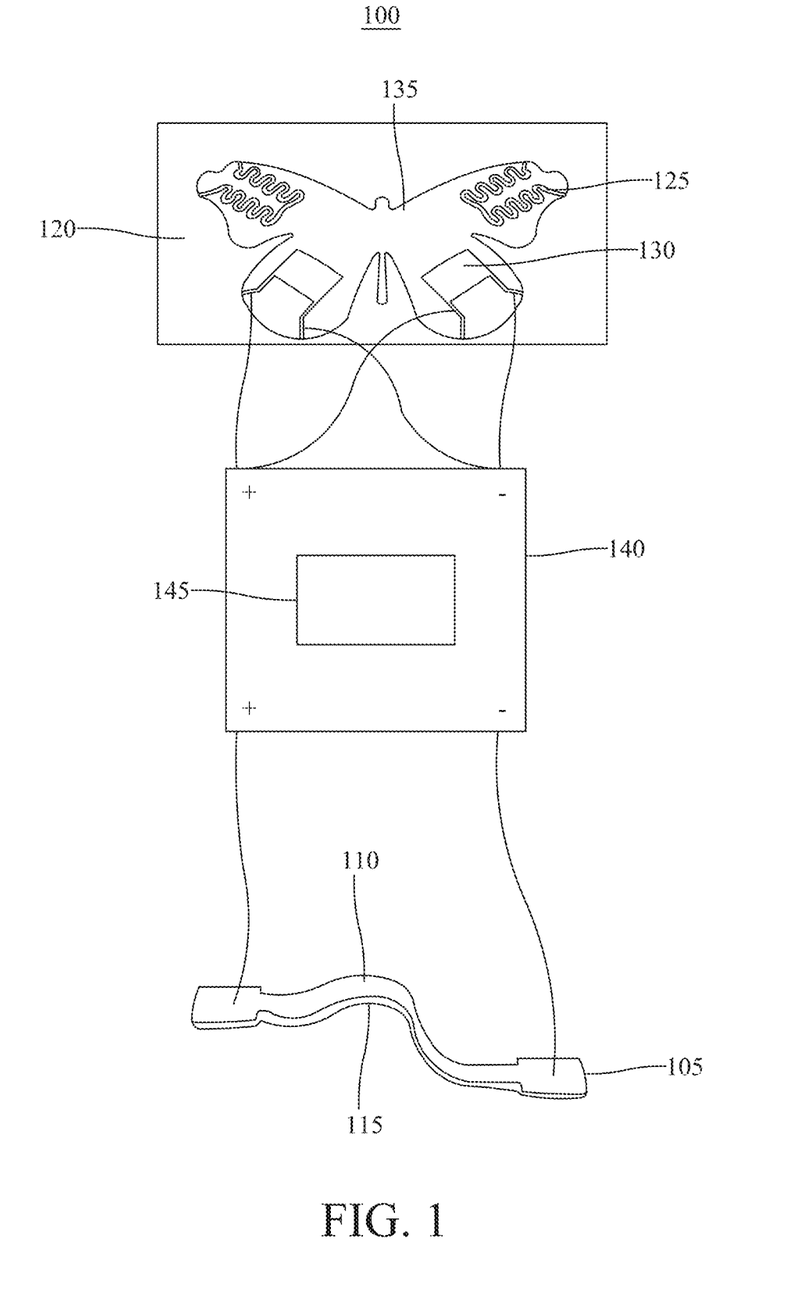
FIG. 1 is a schematic diagram of sensor system according to an embodiment.

FIG. 1 is a schematic diagram of a sensor system 100 having a plant growth sensor 105, which includes a strain sensor 110 arranged on a first stretchable and flexible substrate 115. The sensor system 100 also has an environmental sensor device 120, including first 125 and second 130 environmental sensors arranged on a second stretchable and flexible substrate 135. The sensor system further includes processing electronics 140, which are electrically coupled to the plant growth sensor 105 and the environmental sensor device 120. The processing electronics 140 includes a wireless communication transceiver 145.

In the illustrated embodiment, the first environmental sensor 125 is a capacitive sensor that senses humidity and the second environmental sensor 130 is a resistive sensor that senses temperature. A capacitive humidity sensor is particularly advantageous because it is affected less by changes in temperature than resistive humidity sensors. For ease of illustration, only one of each of the first 125 and second 130 environmental sensors are labeled in FIG. 1. It should be recognized, however, that although FIG. 1 illustrates two of each of the first 125 and second 130 environmental sensors, the environmental sensor device 120 can include only one of each or more than two of each. Further, the environmental sensor device 120 need not have the same number of the first 125 and second 130 environmental sensors.

Although FIG. 1 illustrates the second stretchable and flexible substrate 135 as being in a butterfly shape, the substrate can have any desired shape.

The wireless communication transceiver 145 can perform wireless communications using any wireless communication technique or protocol, including Bluetooth, Wi-Fi, infrared, etc. Other details of the processing electronics 140 will be described below.

Figure 2:
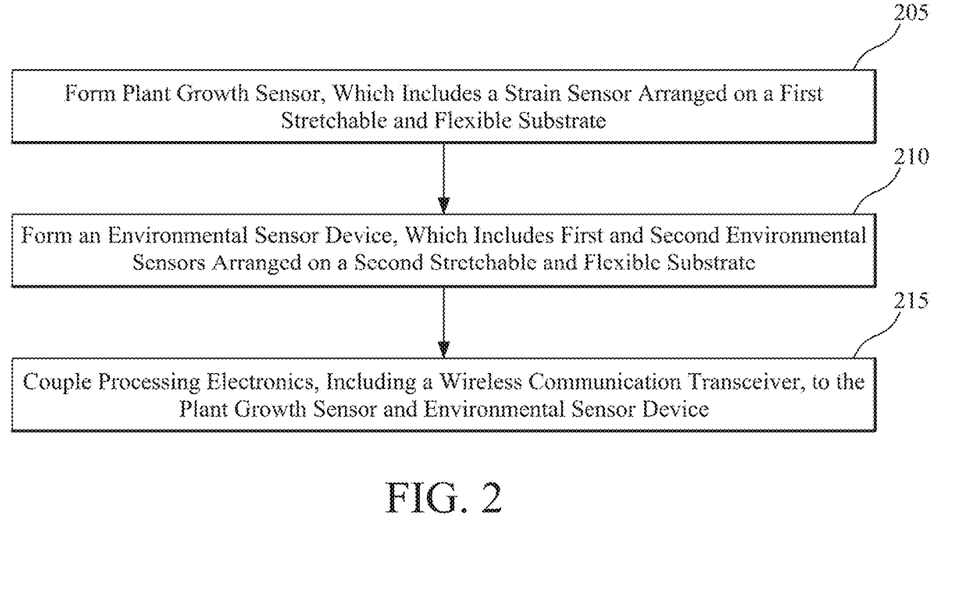
FIG. 2 is a flowchart of a method of producing a sensor system according to an embodiment.
Figure 3:
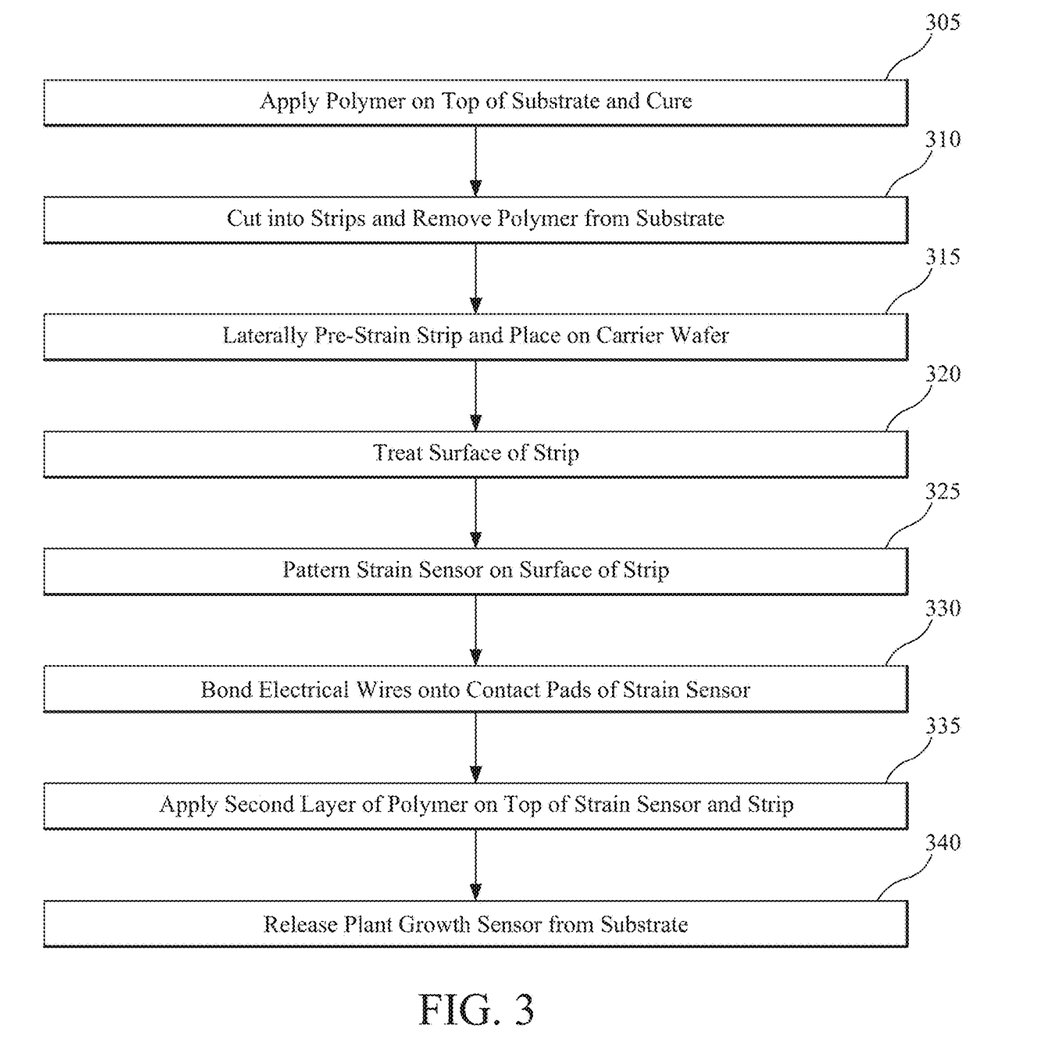
FIG. 3 is a flowchart of a method of producing a plant growth sensor according to an embodiment.

FIG. 2 is a flowchart of a method of producing the sensor system 100. A plant growth sensor 105 is formed (step 205). The plant growth sensor 105 includes a strain sensor 110 arranged on a first stretchable and flexible substrate 115. Also, an environmental sensor device 120 is formed (step 210). The environmental sensor device 120 includes first 125 and second 130 environmental sensors arranged on a second stretchable and flexible substrate 135. The processing electronics 140 are coupled to the plant growth sensor 105 and the environmental sensor device 120 (step 215). The processing electronics 140 includes a wireless communication transceiver 145.

Details of the formation of the plant growth sensor 105 and the environmental sensor device 120 will be described in more detail below.

Although FIG. 2 illustrates steps being performed in a particular order, the environmental sensor device 120 can be formed before the plant growth sensor 105. Further, the processing electronics 140 can be coupled to one of the plant growth sensor 105 and the environmental sensor device 120 prior to forming the other of the environmental sensor device 120 and plant growth sensor 105. Thus, reference to coupling the processing electronics 140 to the plant growth sensor 105 and the environmental sensor device 120 does not require the coupling to be performed at the same time.

Figure 4A:
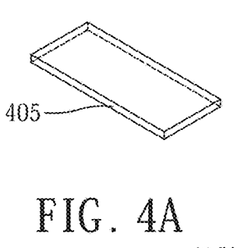
FIGS. 4A-4G are schematic diagrams of a method of producing a plant growth sensor according to an embodiment.

The formation of the plant growth sensor 105 will now be described in connection with FIGS. 3 and 4A-4G. Initially, polymer is applied on top of a substrate and cured (step 305). The substrate can be, for example, a polyethylene terephthalate (PET) substrate. In an embodiment, the polymer can be polydimethylsiloxane (PDMS), which is applied by spin coating, for example, 100 µm of PDMS on the PET substrate. The curing can be performed, for example, at 60° C. for one hour. The cured polymer is then cut into strips and removed from the substrate (step 310). FIG. 4A illustrates one such strip 405. In an embodiment, the strips have, for example, a length of 35 mm and width of 5 mm, and these strips are removed from the substrate by peeling. It should be recognized that polymer strips can be formed in other manners, and thus the strips can be used as the starting point for the method of forming the plant growth sensor.

Figure 4B:
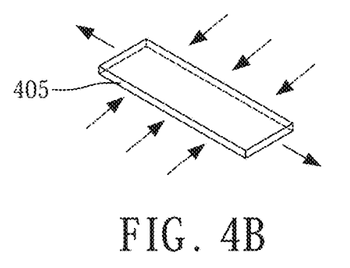

Strip 405 is then pre-strained in the direction in which plant growth will be detected and placed on a carrier wafer (not illustrated) to maintain the pre-strain (step 315 and FIG. 4B). As illustrated in FIG. 4B, the pre-strain applied in the growth detection direction causes the strip to contract in the relatively perpendicular direction, which is a natural result of the pre-straining. In an embodiment, the pre-straining can involve, for example, a 20% tensile stretch. It should be recognized, however, that other percentages of tensile stretch can be employed.

Figure 4C:
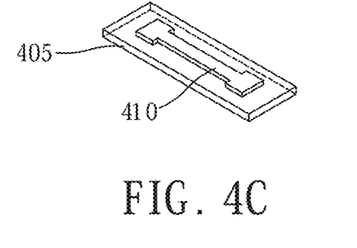

The surface of the pre-strained strip 405 is then treated to temporarily convert it to a hydrophilic material to improve adhesion and the interface with the subsequently formed strain sensor (step 320). The surface treatment is performed to avoid peeling or delamination of the metal strain sensor that will be formed on the treated surface of the pre-strained strip 405. In an embodiment, this is achieved using $O_2$ plasma at low radio frequency power of 60 W for approximately three minutes. A strain sensor 410 is then patterned on a surface of the strip 405 (step 325 and FIG. 4C). The patterning can be achieved, for example, using a shadow mask and then sputtering 10 nm/180 nm of titanium/gold (Ti/Au) on the strip 405. The patterned sensor can, for example, have a length of 25 mm and width of 3 mm.

Figure 4D:
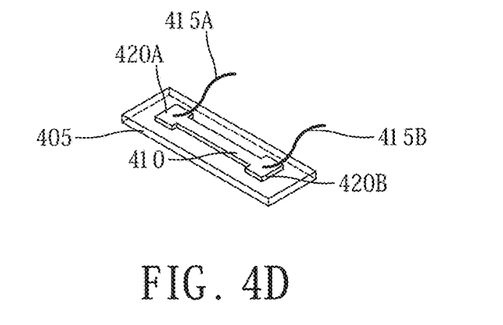

Electrical wires 415A and 415B are then bonded to contact pads 420A and 420B of the strain sensor 410 (step 330 and FIG. 4D). The electrical wires 415A and 415B are preferably lightweight (i.e., light enough not to affect growth when attached to a plant) and can be bonded using, for example, silver epoxy. While pre-strained, a second layer of polymer 425 is then applied on top of the strain sensor 410 and polymer strip 405 as means of packaging (step 335 and FIG. 4E). This can involve, for example, spin coating another 100 µm of PDMS and curing at 60° C. for one hour. The second layer of polymer 425 provides improved control and stability to the strain sensor 410 over numerous cycles of stretching and releasing.

Figure 4E:
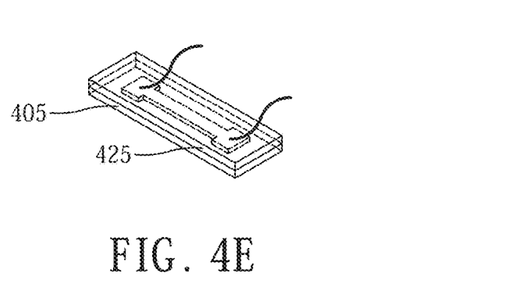

The second layer of polymer 425 puts the strain sensor 410 in a neutral plane of the structure and ensures electrical stability by reducing stresses and uniform distribution of strain in the strain sensor 410 when the sensor is stretched, which provides repeatability of measurements with reduced hysteresis and drift so that the plant growth sensor 105 can be reused. Further, the plant growth sensor is a resistive sensor with resistance measurements varying based on moisture content, and thus this third layer also encapsulates the strain sensor 410 in a hydrophobic material to eliminate the unwanted effects of moisture content on the growth measurements.

Figure 4F:
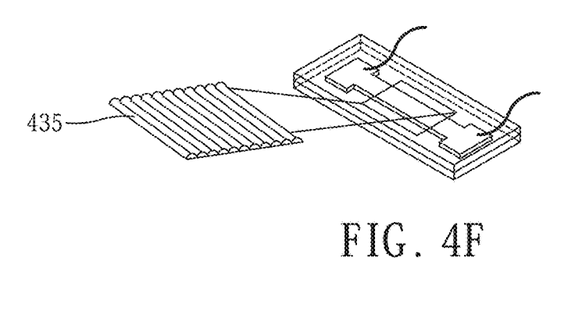

The plant growth sensor 105 is then released from the substrate, which releases the stress of the pre-strain and in turn causes the strain sensor 410 to buckle (step 340). In an embodiment illustrated in FIG. 4F, the strain sensor 410 can have microscale grooves 435 (referred to as "buckled structure") running along the plant growth direction, which enables the strain sensor 410 to stretch and elongate at higher strains without electrical discontinuity. These grooves 435 naturally form once the completely packaged strain sensor 410 is released from the pre-strain and removed from the substrate in step 340.

Figure 4G:
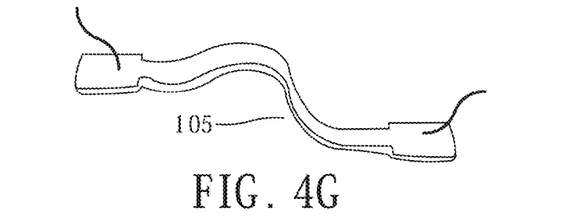

As illustrated in FIG. 4H, the plant growth sensor 105, in the unstrained condition, has a non-planar shape, and more particularly a wave-like shape. These buckles allow the metal of the strain sensor 410 to experience less strain and withstand higher stretching before total discontinuity.

The pre-straining of the polymer during the production of the plant growth sensor 105 provides two main advantages: (i) residual stress release from substrates; and (ii) increased theoretical strain of routings. The release of the pre-straining not only improves stretchability of the strain sensor 410 by providing the non-planar, wave-like shape but also improves the quality of the applied metal material of the strain sensor 410. Because of the different thermal expansion coefficients between the strain sensor 410 and the strip 405 (in the form of a polymer substrate), the surface topography of the sputtered strain sensor 410 has two types of stress: wrinkled (compressive stress) or flat (tensile stress). Macroscopically, wrinkles distribute untidily along the pre-stretched axis, and Y-shaped cracks may occur during sputtering, even when mild heating is used during the processes. Microscopically, the buckled sample is continuous and has a grain-like structure, but the flat sample has randomly arranged microcracks.

Testing demonstrated that a plant growth sensor produced in the manner above can withstand a strain of ~35%, while it exhibits a linear relationship up to approximately 22% strain. This 22% strain corresponds to an elongation of $\Delta L=3.75$ mm, which is more than sufficient to quantitatively and precisely monitor micrometer level length growth of the plant through a given day. In contrast, conventional strain sensors only exhibit linearity up to approximately 8% strain, which does not provide sufficient sensitivity to measure plant growth.

Figure 5:
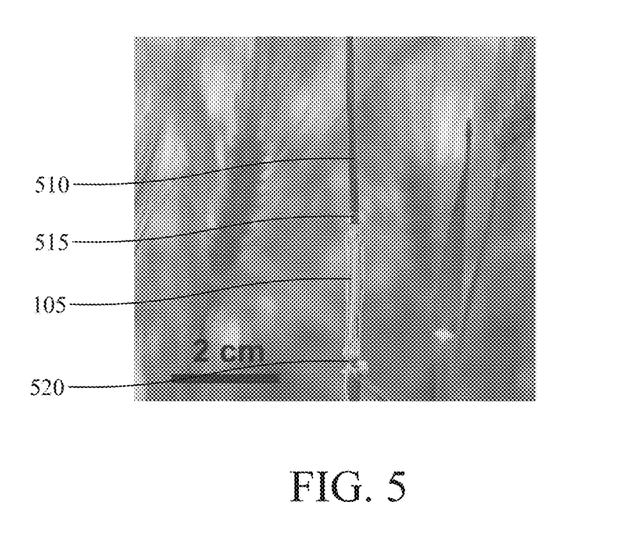
FIG. 5 is a picture of a plant growth sensor attached to a plant according to an embodiment.

FIG. 5 illustrates a plant growth sensor 105 applied to a plant 510, in particular a barley plant. Specifically, the plant growth sensor is applied to one of the plants meristems, which is the region of the plant in which growth is typically manifested. The top 515 and bottom 520 of the plant growth sensor 105 are anchored to the plant 510. Thus, as the plant 510 grows, the plant growth sensor 105 elongates, which changes its resistance. The resistance can then be used to determine the amount of plant growth since the top 515 and bottom 520 are anchored to the plant 510. The processing electronics can store a correlation table between resistance values and corresponding elongations of the plant growth sensor 105. Specifically, after the plant growth sensor 105 is produced, the plant growth sensor can be elongated in regular increments and the resulting resistance values recorded to generate such a correlation table.

A method for producing an environmental sensor will now be described with reference to FIGS. 6 and 7A-7E. Initially, a polymer layer 705 is applied to a silicon wafer 710 and then the polymer layer 705 is cured (step 605 and FIG. 7A). In an embodiment, this is achieved by spin coating 4 µm of polyimide on a silicon (100) substrate and curing at 350° C. The use of polyimide is particularly advantageous because it has high temperature resistance, a low dielectric constant, good mechanical strength and dimensional stability, and a higher affinity towards moisture absorption and desorption.

Figure 6:
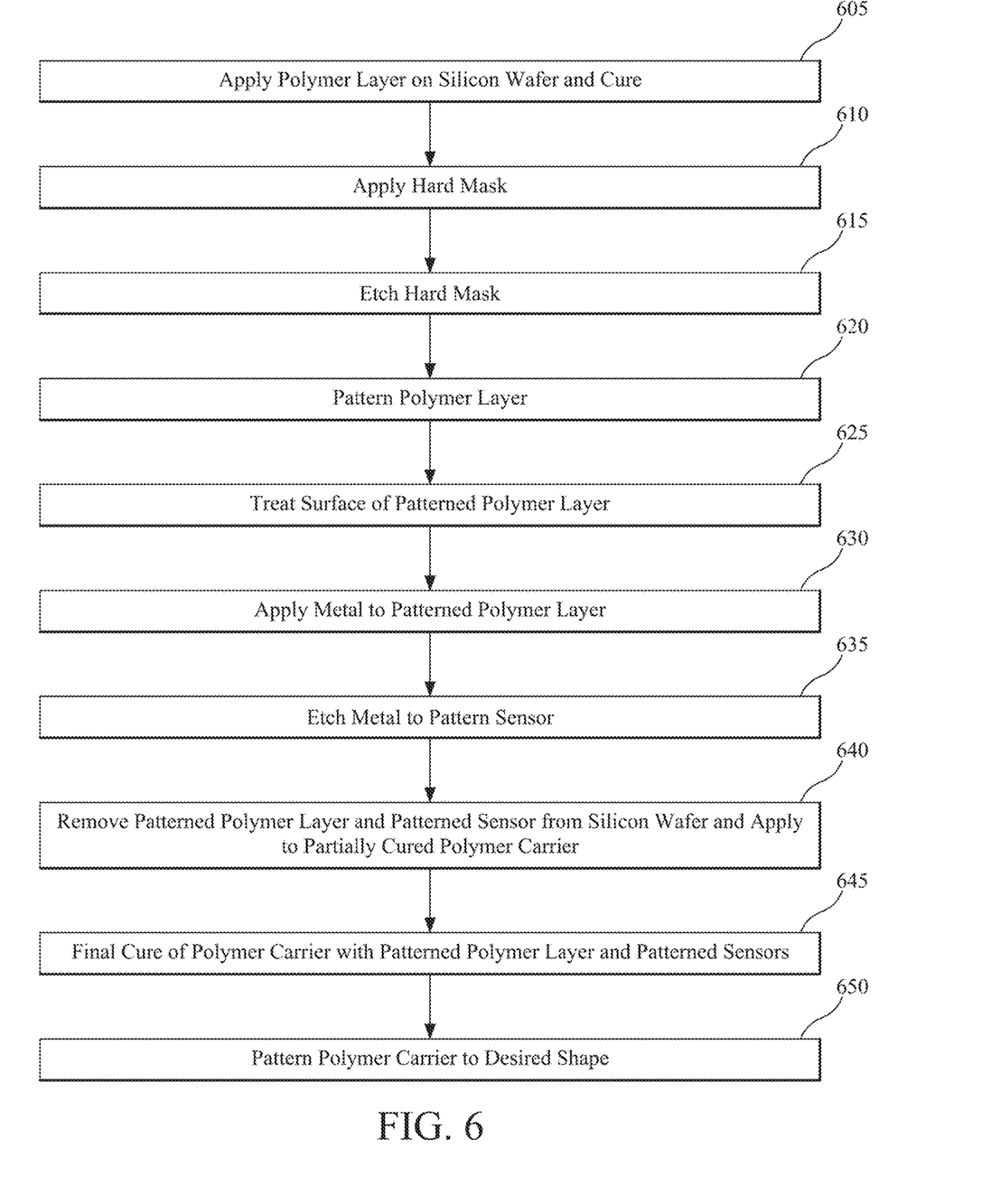
FIG. 6 is a flowchart of a method of producing an environmental sensor device according to an embodiment.
Figure 7A:
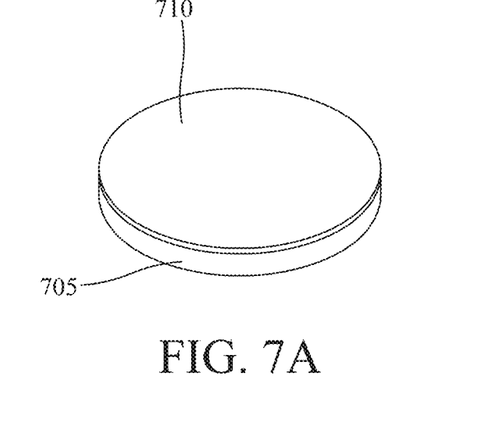
FIGS. 7A-7E are schematic diagrams of a method of producing an environmental sensor device according to an embodiment.
Figure 7B:
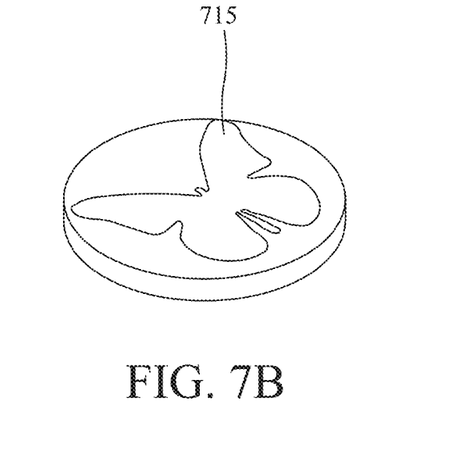

A hard mask is then applied on top of the polymer layer 705 (step 610). In an embodiment, this can involve sputtering 200 nm of aluminum. The hard mask is then etched into the desired geometry for the polymer layer 710 (step 615). In an embodiment, this can involve reactive ion etching (RIE). The polymer layer 710 is then patterned into the desired geometry to form a patterned polymer layer 715 (step 620 and FIG. 7B). In an embodiment, this can be achieved by reactive ion etching using a mix of $O_2$ and $CF_2$, which cleanly patterns the polymer layer 710 into the patterned polymer layer 715.

Figure 7C:
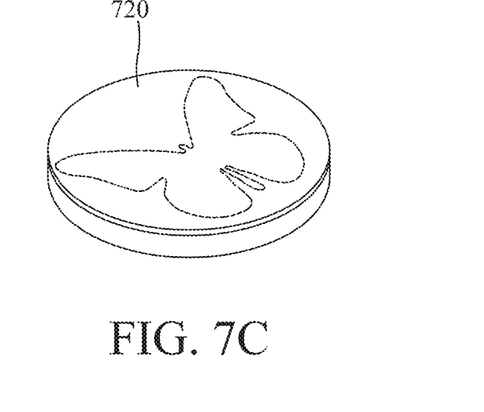

The surface of the patterned polymer layer 715 is then treated to form a treated surface 720 (step 625 and FIG. 7C). The surface treatment is performed to improve adhesion with the metal applied in a subsequent step. In an embodiment, the surface treatment can involve applying $O_2$ plasma for 2 minutes at 60 W. The metal for the sensors is then applied to the patterned polymer layer (step 630) and the metal is then etched to achieve the desired sensor patterns 725-740 (step 635 and FIG. 7D). In an embodiment, the application of the metal can involve sputtering 10 nm/180 nm of titanium/gold (Ti/Au) and the patterning of the metal can involve a reactive ion etching.

Figure 7D:
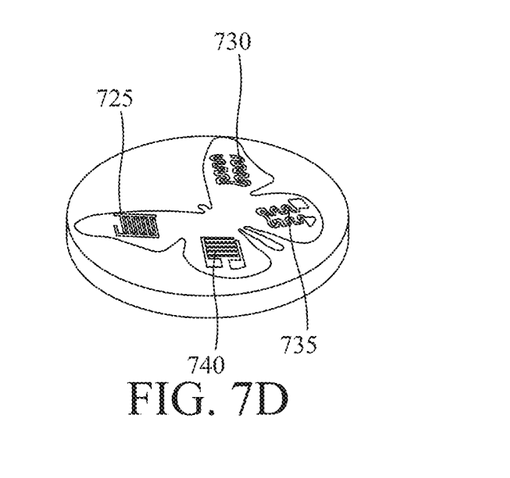

The patterned polymer layer 715 and patterned sensors 725-740 are then removed from the silicon wafer 705 and applied to a partially cured polymer carrier (step 640). In an embodiment, the partially cured polymer layer can be prepared by spin coating a 50 µm thick polydimethylsiloxane (PDMS) layer on a polyethylene terephthalate (PET) wafer, which is then cured at 60° C. for thirty minutes. The polydimethylsiloxane layer ensures the humidity sensor is sensing environmental humidity and not any water vapor transpired through the leaf pores in the plant.

Figure 7E:
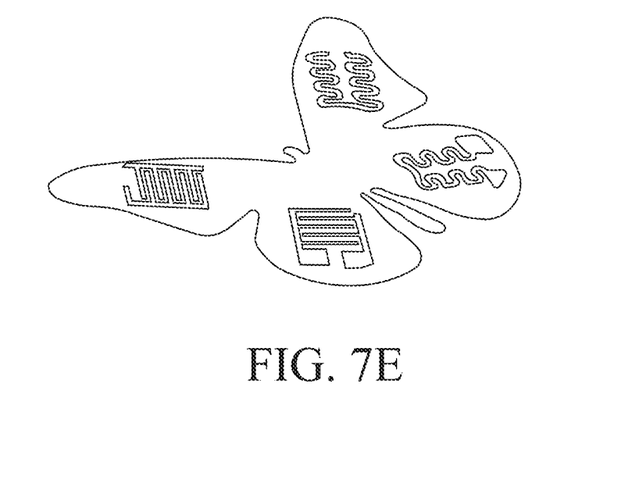

The partially cured polymer layer, carrying the patterned polymer layer 715 and patterned sensors 725-740, is finally cured (step 645). In an embodiment, this can involve curing at 60° C. for thirty minutes. The polydimethylsiloxane is then re-patterned into the desired geometry illustrated in FIG. 7E (step 650). In an embodiment, this re-patterning can be performed manually using, for example, a scalpel or can be automated using, for example a laser.

Testing of the environmental sensor demonstrated that the temperature and humidity sensors provided sufficient sensitivity, while also exhibiting linear responses.

Figure 8:
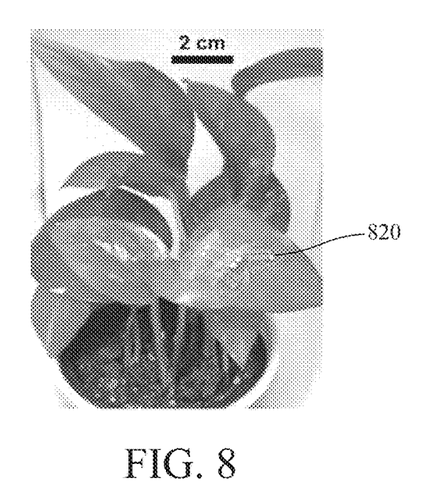
FIG. 8 is a picture of an environmental sensor device attached to a plant according to an embodiment.

FIG. 8 is a picture of an environmental sensor device attached to a plant according to an embodiment. As illustrated, the environmental sensor 820 achieves an intimate adhesion and conformal placement on the surface of a leaf of a plant. Further, as will also be appreciated from the figure, the environmental sensor 820 is lightweight enough not to cause the leaf to deform from its natural position.

The processing electronics will now be described in connection with FIG. 9. The capacitive humidity sensor 925 measures a capacitive output value. Capacitance detector 905 reads the value measured by the capacitive humidity sensor 925 and provides the measured value to memory 910 for storage. The stored value can then be wirelessly communicated from the memory 910 to an external smart device via a wireless communication transceiver 945, which can be, for example, a low power Bluetooth (BLE) transceiver.

The temperature sensor 930 is coupled to a current source 915, which is coupled to a gain stage 920. In the illustrated embodiment, the gain stage 920 includes an operational amplifier 935 having one input coupled to the temperature sensor 930 and the other input coupled as a feedback loop from the output of the operational amplifier 935. The output of the gain stage 920 is coupled to a voltage detector 940, which includes an analog-to-digital converter. The voltage detector provides the detected digital voltage value to memory 910. The memory 910 is coupled to a wireless communication transceiver 945. The wireless communication transceiver 945 allows for remote collection of sensor readings, such as by a person or vehicle (e.g., an unmanned airborne vehicle) having a wireless transceiver capable of communicating with the wireless communication transceiver 945 of the processing electronics. In order to distinguish between readings from different plants, the memory 910 can store a unique identifier that is passed to the device collecting the readings. Alternatively, the reading could be distinguished based on an identifier of the wireless transceiver, such as a medium access control (MAC) identifier.

In an embodiment, the capacitance detector 905 and current source 915 can be part of a programmable system-on-chip (PSoC). This allows the use of, for example, 600 µA of current for the temperature sensor 930, whereas conventionally a Wheatstone bridge is used to convert resistance into voltage. A Wheatstone bridge, however, contains four resistors and consumes a large amount of current and space. For example, a Wheatstone bridge in the circuit of FIG. 9 would require 470 mA, and thus the use of a programmable system-on-chip results in an approximately 99% power savings compared to a Wheatstone bridge. In an embodiment, processing electronics are all components of a programmable system-on-chip, such as the Cypress® (CyBle-222005) 10 mm×10 mm×18 mm Programmable System-on-Chip (PSoC).

Figure 9:
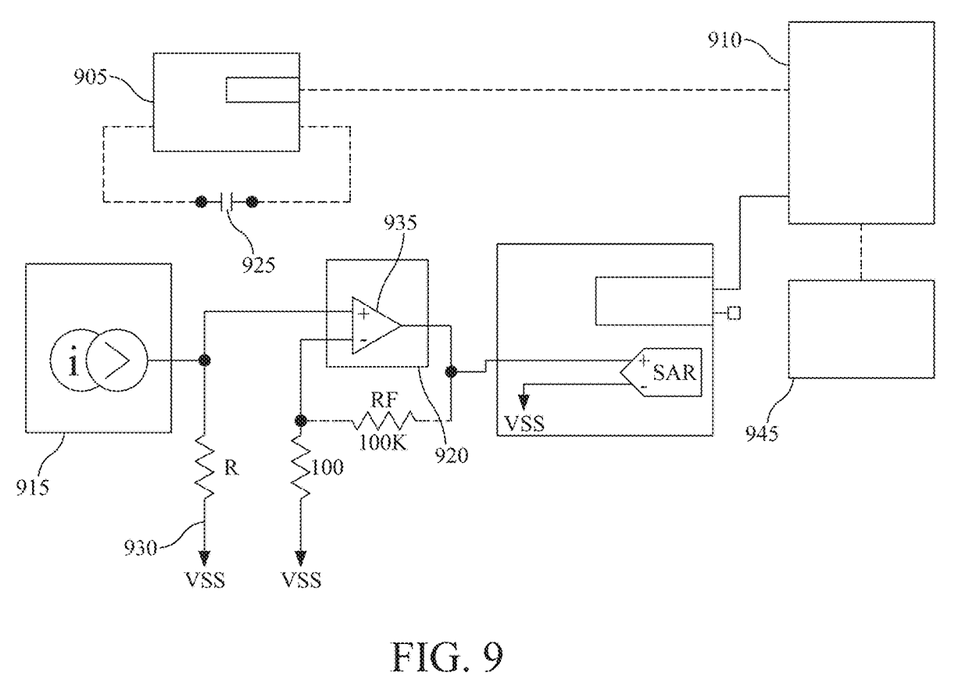
FIG. 9 is a schematic diagram of processing electronics according to an embodiment.

For ease of illustration, the power source for the processing electronics is not depicted in FIG. 9. The power source can be any type of power source, including a wind, solar, and/or battery power source. In an embodiment, the power source is a 3.7 lithium ion battery with a capacity of 500 mAh.

Figure 10A:
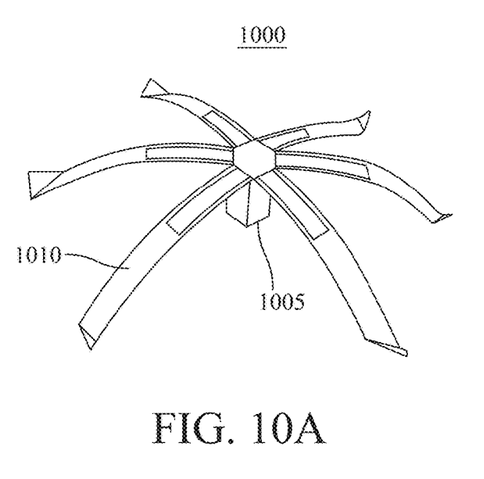
FIGS. 10A-10C are schematic diagrams of a sensor deployment system according to an embodiment.
Figure 10B:
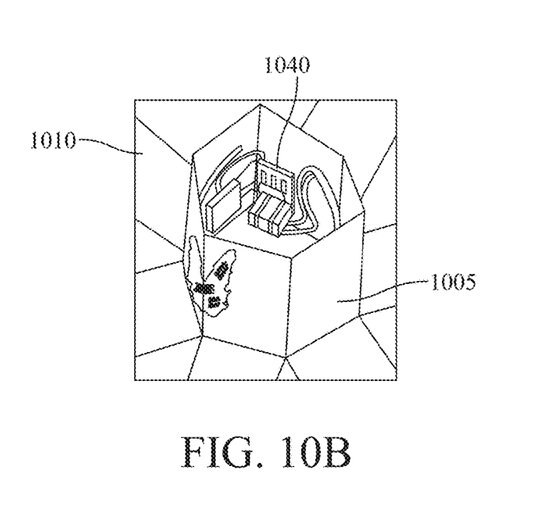
Figure 10C:
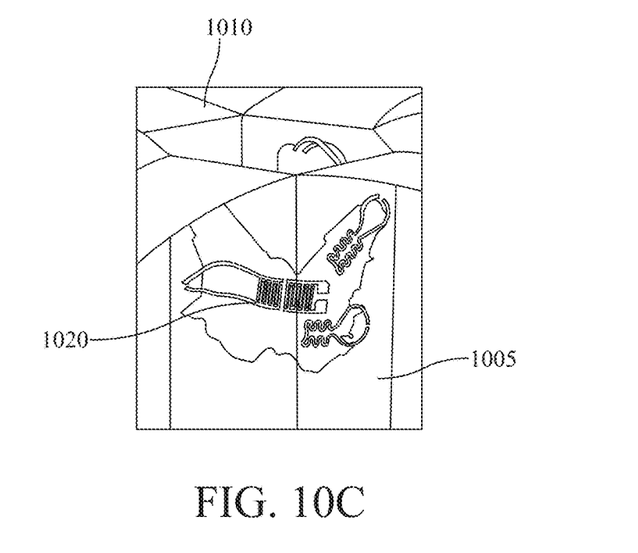

In order to provide localized measurements, the environmental sensors should be arranged more densely within a plant field compared to conventional techniques in which only one or a few sensors are arranged in a plant field. This increased density also increases the costs of manually applying the environmental sensor to the plants. According to an embodiment, a non-powered airborne vehicle can distribute the environmental sensors to the plant field, an example of which is illustrated in FIGS. 10A-10C. The non-powered airborne vehicle 1000 includes a hollow base 1005 and a plurality of wings 1010 (only one of which is labeled in the figures) extending from the hollow base 1005. As illustrated in FIG. 10B, the processing electronics 1040 are arranged on an inner surface of the hollow base 1005. As illustrated in FIG. 10C, the environmental sensor 1020 is arranged on an outer surface of the hollow base 1005. As also illustrated in FIGS. 10B and 10C, the electrical coupling between the environmental sensor 1020 and the processing electronics 1040 are arranged to pass through the hollow base 1005 so as not to affect the flight of the non-powered airborne vehicle 1000.

The non-powered airborne vehicle 1000 has a similar design to flying seeds in nature, which are able to twirl and fly in a seamless and stable trajectory. In order to achieve similar behavior, the hollow base 1005 is designed to be slightly heavier than the winglets because it acts as the center of mass of the non-powered airborne vehicle 1000, thus providing a way to balance, control, and stabilize the trajectory of the non-powered airborne vehicle 1000. Without a heavier base, a non-powered airborne vehicle with this design can be diverted from its original path, fly in a random fashion, and twirl upside down.

Figure 11:
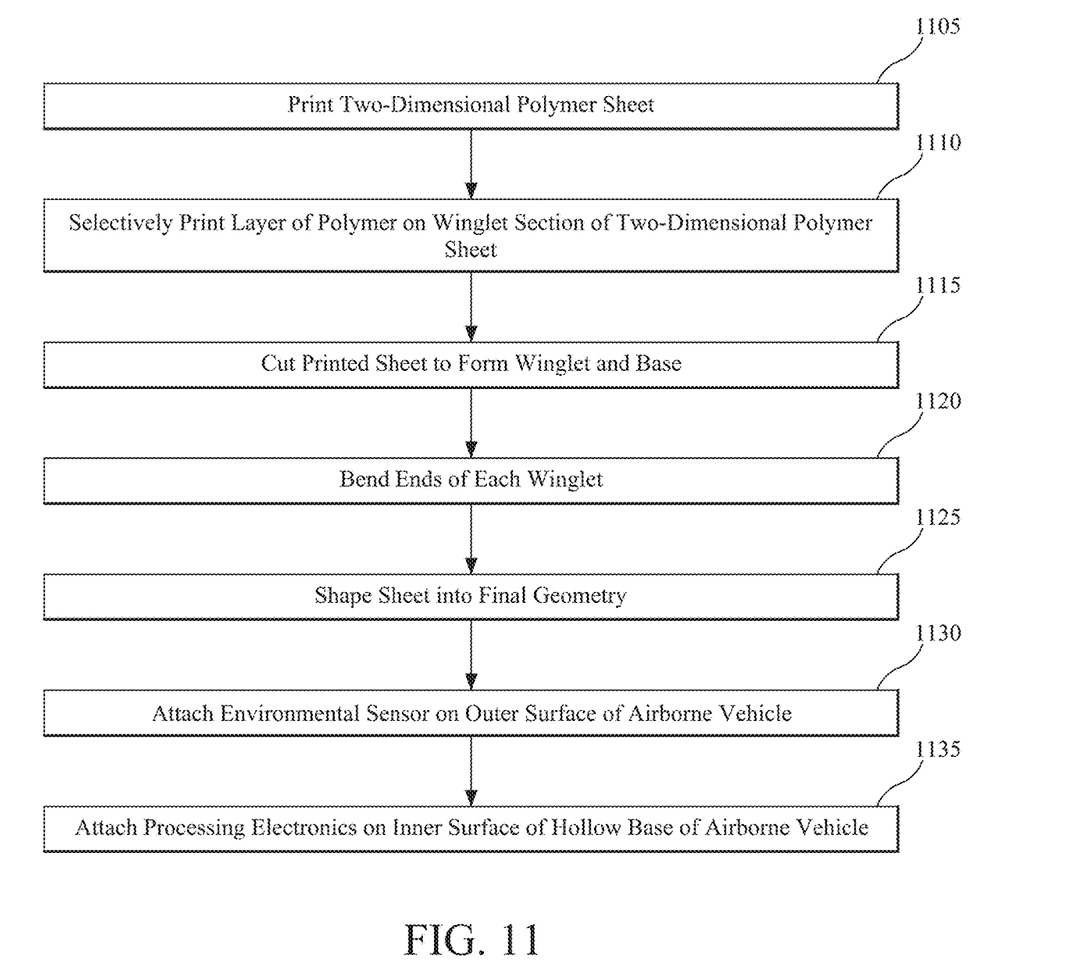
FIG. 11 is a flowchart of a method of producing an airborne vehicle for a sensor deployment system according to an embodiment.
Figure 12A:
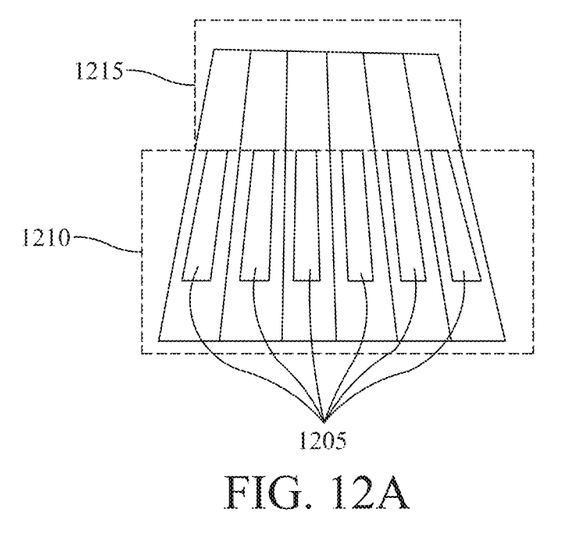
FIGS. 12A-12D are schematic diagrams of a method of producing an airborne vehicle for a sensor deployment system according to an embodiment.

A method for making the non-powered airborne vehicle 1000 will now be described in connection with FIGS. 11 and 12A-12D. Initially, a two-dimensional polymer sheet is printed (step 1105). In an embodiment, the two-dimensional sheet is 17 cm long and 12 cm wide. As illustrated in FIG. 12A, the printing includes printing lines along the polymer sheet as demarcation lines between each winglet, which lines can be used to guide the subsequent cutting process. In an embodiment, the polymer sheet is comprised of acrylonitrile butadiene styrene (ABS), which is particularly advantageous due to its lower density compared other polymer materials (e.g., polylactic acid or polylactide), and hence results in higher lifting force compared to other polymer materials. A layer of polymer 1205 is then selectively printed on the winglet section 1210 of the two-dimensional polymer sheet 1215 (step 1110 and FIG. 12A). In an embodiment, the layer of polymer 1205 is, for example, 5 cm by 1 cm.

Figure 12B:
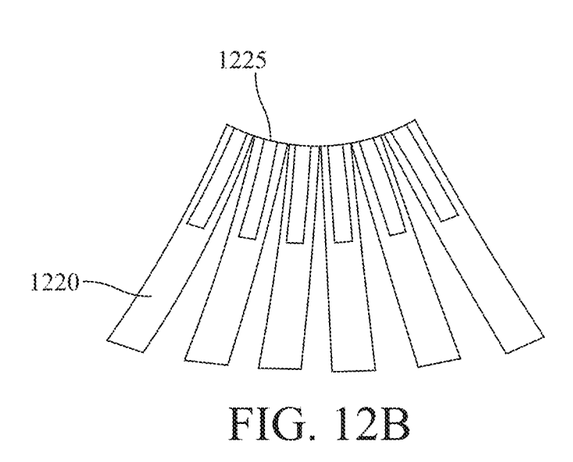

The printed two-dimensional polymer sheet is then cut to form the winglets 1220 and base 1225 (step 1115 and FIG. 12B). In an embodiment using a two-dimensional sheet that is 17 cm long and 12 cm wide, the length of the base is 5 cm, the length of the winglets is 12 cm, and the width of each of the winglets is 2 cm.

Figure 12C:
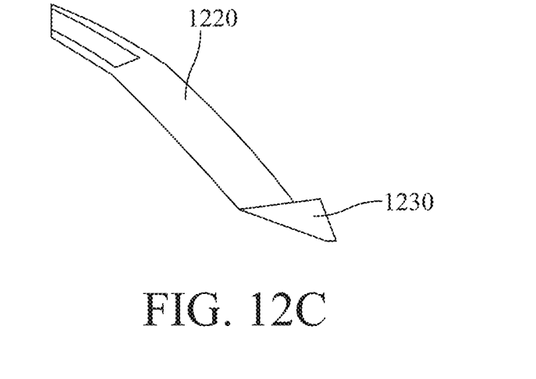
Figure 12D:
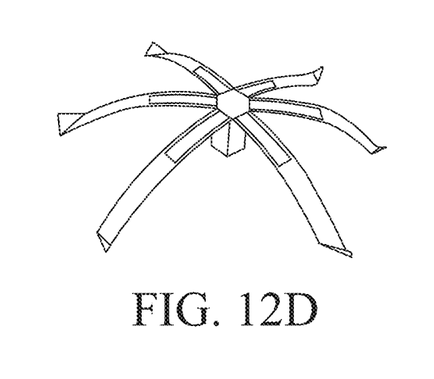

The ends 1230 of each of the winglets 1220 are bent upwards at a shifted angle (step 1120 and FIG. 12C). The bending of the ends 1230 of each of the winglets 1220 generates a smaller vortex around the tips of the winglets, which helps reduce drag force and allows for more twirling while the non-powered airborne vehicle 1000 is airborne. In an embodiment, the ends 1230 of each of the winglets 1220 is bent upwards at a 45° angle at approximately 1 cm from the end 1230. The printed two-dimensional polymer sheet is then shaped into the final geometry of the non-powered airborne vehicle (step 1125 and FIG. 12D).

An environment sensor is then attached on an outer surface of the non-powered airborne vehicle (step 1130) and processing electronics are attached to an inner surface of the hollow base of the airborne vehicle (step 1135).

As an alternative to the method described above, the non-powered airborne vehicle can be produced using three-dimensional printing or other techniques.

The disclosed embodiments provide a sensor system, method of production, and sensor deployment system. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A sensor system, comprising:
    a plant growth sensor, including a strain sensor arranged on a first stretchable and flexible substrate;
    an environmental sensor device, including first and second environmental sensors arranged on a second stretchable and flexible substrate; and
    processing electronics electrically coupled to the plant growth sensor and the environmental sensor device, wherein the processing electronics include a wireless communication transceiver,
    wherein the first stretchable and flexible substrate and the strain sensor have a non-planar shape when the plant growth sensor is not applied to a plant.

2. The plant growth sensor of claim 1, wherein the non-planar shape is a wave-like shape.

3. The plant growth sensor of claim 1, wherein the first and second stretchable and flexible substrates are polydimethylsiloxane (PDMS).

4. The plant growth sensor of claim 1, wherein the strain sensor is metallic.

5. The sensor system of claim 1, wherein the first environmental sensor is a temperature sensor and the second environmental sensor is a humidity sensor.

6. The sensor system of claim 5, wherein the temperature sensor is a resistive sensor comprising metal.

7. The sensor system of claim 5, wherein the humidity sensor is a capacitive sensor comprising metal.

8. The sensor system of claim 6, wherein the processing electronics include a current source coupled to the temperature sensor.

9. The sensor system of claim 8, wherein the processing electronics further comprise a capacitance detector coupled to the humidity sensor.

10. The sensor system of claim 9, wherein the current source and capacitance detector are components of a programmable system-on-chip.

11. A method of producing a sensor system, the method comprising:
    forming a plant growth sensor, which includes a strain sensor arranged on a first stretchable and flexible substrate;
    forming an environmental sensor device, which includes first and second environmental sensors arranged on a second stretchable and flexible substrate; and
    coupling processing electronics to the plant growth sensor and the environmental sensor device, wherein the processing electronics includes a wireless communication transceiver.

12. The method of claim 11, wherein the formation of the plant growth sensor comprises:
    pre-straining the first stretchable and flexible substrate;
    applying the strain sensor on the stretched, first stretchable and flexible substrate; and
    releasing the first stretchable and flexible substrate from the pre-strain.

13. The method of claim 11, wherein the formation of the environmental sensor device comprises:
    forming the first and second environmental sensors on a carrier;
    transferring the first and second environmental sensors from the carrier to the second stretchable and flexible substrate, wherein the second stretchable and flexible substrate is partially cured; and
    completing curing of the second stretchable and flexible substrate after the first and second environmental sensors are transferred to the second stretchable and flexible substrate.

14. The method of claim 13, wherein prior to forming the first and second environmental sensors on the carrier, the method comprises:
    treating a surface of the carrier to improve adhesion of the first and second environmental sensors with the carrier.

15. A sensor deployment system, comprising:
an airborne vehicle, comprising a hollow base and a plurality of wings extending from a top portion of the hollow base, wherein the hollow base and the plurality of wings are monolithic;
an environmental sensor device arranged on an outer surface of the hollow base, wherein the environmental sensor device includes first and second environmental sensors arranged on a stretchable and flexible substrate; and
processing electronics arranged on an inner surface of the hollow base, wherein the processing electronics are coupled to the environmental sensor device and the processing electronics includes a wireless communication transceiver.

16. The sensor deployment system of claim 15, wherein the airborne vehicle is a non-powered airborne vehicle.

17. The sensor deployment system of claim 15, wherein the first environmental sensor is a temperature sensor and the second environmental sensor is a humidity sensor.

18. The sensor deployment system of claim 17, wherein the temperature sensor is a resistive sensor comprising metal.

19. The sensor deployment system of claim 18, wherein the humidity sensor is a capacitive sensor comprising metal.

* * * * *